United States Patent [19]

Koashi et al.

[11] Patent Number: 5,097,130
[45] Date of Patent: Mar. 17, 1992

[54] QUANTITATIVE DETERMINATION METHOD OF CHEMICALS FOR PROCESSING SEMICONDUCTOR AND AN APPARATUS THEREOF

[75] Inventors: Katsue Koashi, Toyonaka; Hiroshi Yokota, Izumi; Naoki Yanai, Hirakata, all of Japan

[73] Assignee: Kurashiki Boseki Kabushiki Kaisha, Kurashiki, Japan

[21] Appl. No.: 584,663

[22] Filed: Sep. 19, 1990

[30] Foreign Application Priority Data

Sep. 20, 1989 [JP] Japan .................................. 1-245977
Aug. 31, 1990 [JP] Japan .................................. 2-232190

[51] Int. Cl.⁵ .......................................... G01N 21/35
[52] U.S. Cl. ...................................... 250/339; 250/343
[58] Field of Search ............ 200/339, 341, 343, 338.4

[56] References Cited

U.S. PATENT DOCUMENTS

| 3,947,124 | 3/1976 | West | 250/458.1 |
| 4,730,112 | 3/1988 | Wong | 250/343 |
| 4,805,623 | 2/1989 | Jöbsis | 250/339 |

FOREIGN PATENT DOCUMENTS

0317121  5/1989  European Pat. Off. .

Primary Examiner—Carolyn E. Fields
Assistant Examiner—Drew A. Dunn
Attorney, Agent, or Firm—Armstrong, Nikaido, Marmelstein, Kubovcik & Murray

[57] ABSTRACT

The present invention relates to a quantitative determination method of a medicament for processing semiconductor by near-infrared spectrometry at 800–1400 μm and an apparatus which is adapted to the practice of said method. According to the present invention, concentration of an aqueous solution of the medicament can be determined without drawbacks of the prior methods.

2 Claims, 12 Drawing Sheets

Near-infrared spectra of NH4OH-H2O2-H2O system $$\begin{pmatrix} 1: 4\% NH_4OH + 1.5\% H_2O_2 \\ 2: 3\% NH_4OH + 1.5\% H_2O_2 \\ 3: 2\% NH_4OH + 1.5\% H_2O_2 \end{pmatrix}$$

Fig. 9

Near-infrared spectra of $H_2O_2$-$NH_4OH$-$H_2O$ system $$\begin{pmatrix} 1: & 24.2\% H_2O_2 + 7.5\% NH_4OH \\ 2: & 16.2\% H_2O_2 + 7.5\% NH_4OH \\ 3: & 7.3\% H_2O_2 + 7.5\% NH_4OH \\ 4: & 1.5\% H_2O_2 + 7.5\% NH_4OH \\ 5: & 0\% H_2O_2 + 7.5\% NH_4OH \end{pmatrix}$$

Fig. 10

Near-infrared spectra of $H_2SO_4$-$H_2O_2$-$H_2O$ system

QUANTITATIVE DETERMINATION METHOD OF CHEMICALS FOR PROCESSING SEMICONDUCTOR AND AN APPARATUS THEREOF

BACKGROUND OF THE INVENTION

1. Field of the Invention

The present invention relates to a quantitative determination method of chemicals for processing semiconductor, and more particularly, to quantitative analysis of the chemicals by near-infrared spectrometry at 800–1400 nm and an apparatus therefor.

2. Prior art

In a field of semiconductors it is a problem to be solved to determine the concentration of an aqueous solution of the chemicals for processing a semiconductor by an accurate, easy and rapid method.

With respect to treating chemicals such as acids (sulfuric acid, hydrochloric acid, nitric acid, hydrofluoric acid and the like), alkaline solutions (aqueous solution of ammonium and the like), solution of redox material (aqueous solution of hydrogen peroxide and the like) and the like which are used in a washing process of silicon wafer, photoetching process and the like, automation of chemical analysis and supply of the treating chemicals is required from the viewpoints of yield increase of product, safety, working efficiency and the like.

Heretofore, titration method, electrolysis method at constant potential and analytical method using electrodes such as redox electrodes, electrodes for selecting ions and the like are employed for this purpose.

However, the concentration cannot be determined in a short time by the titration method; stable measurement cannot be carried out for a long time by the electrolysis method because surfaces of electrodes are contaminated and the temperature of the sample to be determined is changed during measurement; therefore it is necessary for the method not only to adjust the concentration and pH of the sample to suitable ranges but also to add a standard into the sample.

SUMMARY OF THE INVENTION

An essential object of the present invention is to provide a method for determining a concentration of an aqueous solution of the chemicals for processing semiconductor accurately, easily and rapidly without the aforementioned drawbacks of the prior methods.

According to the present invention, there is provided a quantitative method for determining the concentration of chemicals used for processing semiconductor which comprises measuring the near-infrared spectrum at 800–1400 nm of an aqueous solution of chemicals of which concentrations are known, determining absorbances at wavelengths at which significant differences of absorption bands between said spectrum and a near-infrared spectrum of pure water at 800–1400 nm are given, deriving a following calibration equation (I) from regression analysis of a relation between said concentration and absorbance, and determining a concentration of chemicals sample by using the calibration equation (I):

$$C = \Sigma a_i A_i \quad (I)$$

where C is the concentration of the chemicals sample, $A_i$ is absorbance at $\lambda_i$ whereat said absorption bands are given, $a_i$ is a constant empirically determined according to the system, $\lambda_i$ and numbers of $\lambda_i$ which are used in order to derive the calibration equation (I).

DETAILED DESCRIPTION OF THE INVENTION

The above-mentioned quantitative method essentially differs from hitherto generally used quantitative method wherein concentration of sample is determined based on infrared characteristic absorption.

Inorganic electrolytes such as acids, alkalis, salts and the like dissociate into positive and negative ions in their aqueous solutions. The negative side of the water dipole is oriented toward positive ions and the positively charged side of the water dipole is oriented toward negative ions (ionic hydration). The 6 bonding state of the water molecule itself and the bonding state between hydrogen-bonded water molecules are influenced by dissociation and strain of hydrogen bond between water molecule near the ions formed by ionic hydration and water molecule in the bulk as well as polarization change of water molecule by ionic electric field. Accordingly, near-infrared spectrum of water in the aqueous solutions of inorganic electrolytes differs from that of pure water.

In other words, as the near-infrared spectrum of water is changed by ionic hydration, it is possible to determine concentrations of ionic species indirectly by investigating degree of the spectrum changes. Therefore, infrared characteristic spectra of ionic species are not necessary for this quantitative determination.

Accordingly, it is possible to determine the concentration of each ionic species in the sample containing mixed ionic species because each ionic species gives inherent near-infrared spectrum.

In order to derive aforesaid calibration equation (I), it is necessary to compare near-infrared spectrum (800–1400 nm) of an aqueous solution of the chemicals for processing semiconductor with that of pure water and to select wavelengths at which remarkable significant difference of absorption bands between both is given. For this purpose, it is convenient to utilize difference spectrum obtained by subtracting near-infrared spectrum of pure water contained in the aqueous solution of the chemicals of which concentration is relatively high from that of the aqueous solution. The difference spectrum is regarded as the sum of spectrum of solute and that attributed to an interaction of the solute and water. Therefore, wavelengths at which characteristic difference spectra are given can easily be selected by investigating the difference spectra.

These wavelengths are selected from those at which the spectra bring about a remarkable change in accordance with concentration change of a specific component and the spectra are not subject to a great influence of disturbance and interference of other components, said wavelengths being in near-infrared region wherein characteristics bands of water are remarkably dominated.

Numbers of the selected wavelengths are determined in consideration of kinds of the components contained in the sample solution, numbers of wavelengths at which significant difference of absorption bands is observed, variable factors of the sample and a measuring apparatus, measuring accuracy and the like. It is to be desired that at least three wavelengths should be selected in the region of characteristic bands of water. Usual numbers of wavelengths to be selected are the sum of numbers of main components which are variable in the sample and additional further wavelengths. The close wavelengths which are in the range of the half width of a commercial interference filter should not be selected.

As a characteristic band of water, there are 0.96 μm band, 1.15 μm band, 1.43 μm band and 1.93 μm band. It is said that the spectrum is the one wherein band shape having three peaks in each band region are composited. Although the limits of each band region is unclear, the wavelengths are selected in the range of from 800 nm to 1400 nm in the present invention.

In case of simultaneous determination of plural components contained in mixed samples, it is ideal to use exclusively an optimum set of wavelengths for each component. However, such a combination of the set is unpractical because many interference filters are necessary for a spectroscope. For the sake of simplifying the design of the filter instruments, the same set of wavelengths is applied to each component.

Subsequently, near-infrared spectra of reference samples of which concentrations are known and measured at 800–1400 nm, absorbances at wavelengths selected as stated above are determined, and relationship between said concentrations and absorbances is obtained by the regression analysis.

In other words, calibration curve of which evaluation function for quantitative accuracy is constructed by means of the calibration set of a samples, the performance of said calibration curve is verified by means of verification set of samples of which concentrations are known, and the calibration curve and the selected wavelengths which produces the best accuracy is determined by repeating the construction of said calibration curve and the verification of said performance.

According to the aforesaid procedures, the calibration equation (I) can be obtained:

$$C = \Sigma a_i A_i \quad (I)$$

where C is the concentration of the chemicals for processing semiconductor, $A_i$ is absorbance at $\lambda_i$ whereat aforementioned significant difference of absorption bands is given, $a_i$ is constant determined by kind of the chemicals, $\lambda_i$ and number of $\lambda_i$ which are used in order to derive the calibration equation (I). Correction term may be introduced into the calibration equation (I) according to the samples (cf. Example 4).

Therefore concentration of a sample solution can be predicted accurately, easily and rapidly by measuring nearinfrared spectrum of the sample solution of which concentration is unknown at 800–1400 nm and substituting absorbance of the absorption band at $\lambda_i$ for $A_i$ of the calibration equation (I).

Measurements of plural chemicals for processing semiconductor can be carried out by obtaining a calibration equation for each component of the sample solution. For example, concentration of each component of the following mixed samples is used in the field of semiconductor: $H_2SO_4$—$H_2O_2$, $HCl$—$H_2O_2$, $NH_3$—$H_2O_2$, $HNO_3$—$HCl$, $HF$—$NH_4F$.

Figure 1:
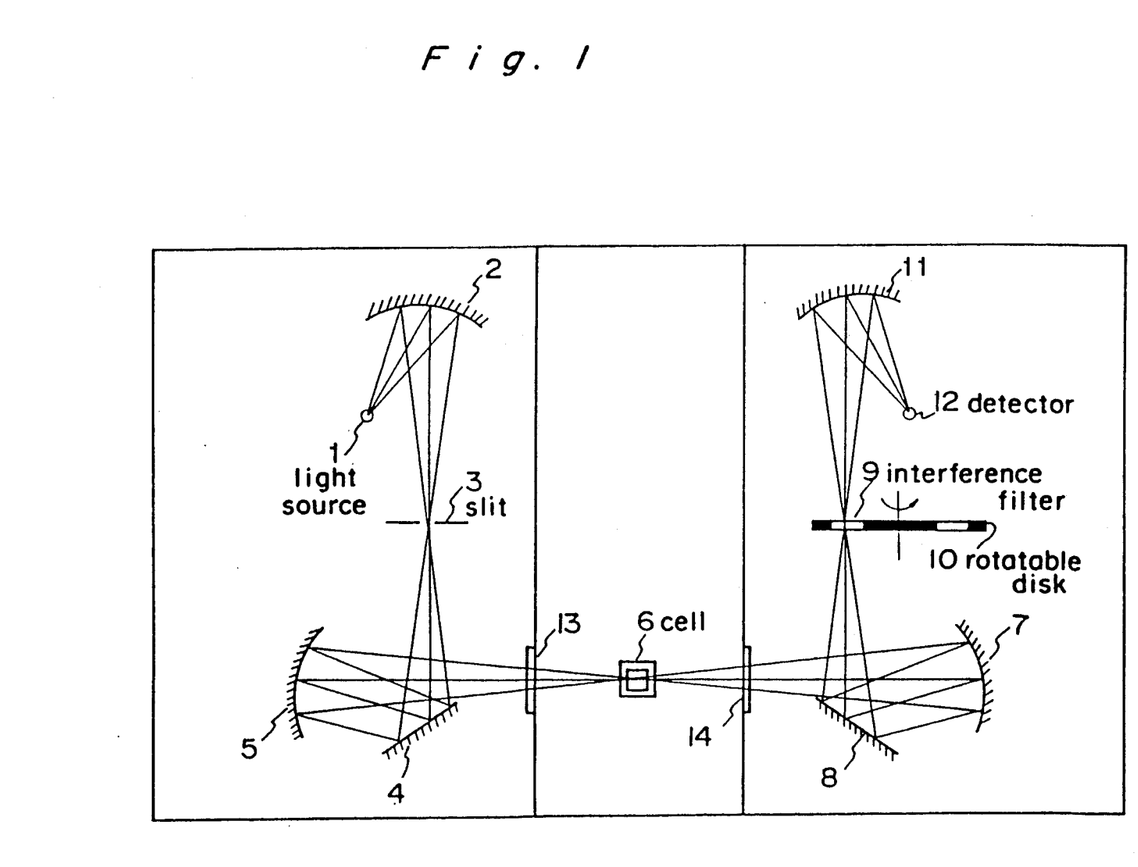
FIG. 1 schematically illustrates an apparatus which is adapted to the practice of the above-mentioned method of the present invention.

An analytical apparatus which is adapted to the practice of the above-mentioned quantitative method of the present invention will be illustrated with reference to the accompanying drawing.

FIG. 1 schematically illustrates an embodiment of the apparatus. The quantitative apparatus shown in FIG. 1 comprises a light source 1, a concave reflex mirror 2 which reflects light emitted from the light source 1, a slit 3 which collects reflected light from the concave reflex mirror 2, a plane reflex mirror 4 which reflects light emitted from the slit 3, a concave reflex mirror 5 which collects reflected light from the plane reflex mirror 4, a concave reflex mirror 7 which reflects light from a cell 6, a plane reflex mirror 8 which reflects light from the concave reflex mirror 7, a rotatable disk 10 provided with a interference filters 9 through which only light having a fixed wavelength, passes a concave reflex mirror 11 which reflects reflected light from the plane reflex mirror 8 collected by the interference filter 9, and a detector 12 which collects reflected light from the concave reflex mirror 11.

Emitted light from the light source 1 such as tungsten-halogen lamp is focalized on the slit 3, the position of the slit being point source of light. The light beam passed through the slit 3 is collected on the position of the cell 6 through a side window 13 of the light source part by way of the plane reflex mirror 4 and the concave reflex mirror 5. The light beam passed through the cell 6 is converged on the interference filter 9 located on the rotatable disk 10 through a side window 14 of the detection part by way of the concave reflex mirror 7 and plane reflex mirror 8.

The side window 13 and 14 are usually made of fused quartz in order to isolate from an atmosphere of the cell part. A flow cell made of fused quartz is usually used as the cell 6, said cell being connected to a sampling line (not shown). The sample flows into the cell at a constant rate and flows out the cell after measurement. Optimum pass length of the cell 6 in near-infrared region is of the order of 1–10 mm based on absorbance of water. Said order of pass length is favorable from the view points of contamination, clogging and cleaning of the cell.

The interference filter 9 is a narrow bandpass filter though which only the light having specific wavelength can be passed. Previously selected numbers (E.G. six) of the interference filters are distributed on the rotatable disk 10 and the interference filters and change successively with a rotation of the rotatable disk.

The light beam having specific wavelength $\lambda_i$ passed through the interference filter 9 is collected on the detector 12 by way of the concave reflex mirror 11. It is convenient to use germanium detector as the detector 12. Signals from the detector 12 corresponding to the specific wavelength $\lambda_i$ are converted into transmittance after subjected to dark current correction and blank correction, said transmittance being then converted into the absorbance $A_i$ of the calibration equation (I).

According to the present invention, concentration of the chemicals for processing semiconductor can be determined safely, accurately, easily and rapidly by measuring near-infrared spectrum caused by an ionic hydration, said chemicals being inorganic electrolytes providing no infrared characteristic bands which have been utilized for qualitative and quantitative determination of organic compounds.

The present invention will now be described by way of examples.

EXAMPLE 1

Quantitative determination of ammonia-hydrogen peroxide

An aqueous solution of mixture of ammonia and hydrogen peroxide is a typical alkaline cleaning fluid which is used to remove silicon surface by etching. Hydrogen peroxide is used as an oxidizing agent to suppress a solvency action of the aqueous solution. Cleaning effect of the aqueous solution is such that the removing rate of silicon particle whose diameter is 1 $\mu$m is 95-98% when the silicon surface is immersed in the aqueous solution ($NH_4OH:H_2O_2:H_2O = 1:2:13$) at 80° C. for 10 minutes. However, if this cleaning fluid is used at high temperature, the concentration of the fluid decreases to 50% within less than 20 minutes and the cleaning effect lowers because of drastic vaporization of ammonia and decomposition of hydrogen peroxide. Accordingly, the cleaning fluid one made cannot be used repeatedly for several times. Usually, freshly prepared cleaning fluid is substituted for the used solution after 30-40 minutes. But usable time of the cleaning solution may be prolonged by replenishing the exhausted amounts of the solution. For this reason, it is requested that the cleaning effect is maintained and controlled at a constant level by monitoring a mixing ratio of the cleaning fluid and a deterioration thereof with the passage of time.

PREPARATION OF SAMPLES

In order to verify the performance of the calibration equation for quantitative determination, calibration set of samples and verification set of samples were prepared whose concentrations encompass range used in the industrial process for cleaning semiconductor. Eighteen calibration samples and 18 verification samples, in which concentrations of $NH_4OH$ and $H_2O_2$ are 0-3 wt % and 0-10 wt % respectively and ratios of the components are different from each other, were prepared by diluting aqueous ammonia whose concentration (21.65%) is confirmed by pH titration using dilute sulfuric acid with hydrogen peroxide solution whose concentration (34.95%) is confirmed by titration using sodium thiosulfate.

DERIVATION OF THE CALIBRATION EQUATION

The following calibration equations are obtained according to the aforementioned derivation procedure of the calibration equation:

For $NH_4OH$
$C = -17.75 A_1 + 3.50A_2 + 0.61A_3 - 11.91A_4 - 19.50A_5 - 45.06A_6$
For $H_2O_2$
$C = 40.24A_1 + 82.33A_2 - 19.61A_3 - 80.18A_4 + 10.20A_5 - 32.98A_6$

In the above calibration equations, $A_1-A_6$ are absorbances at wavelengths $\lambda_1-\lambda_6$ corresponding to the absorption bands which give significant differences in comparison with that of near-infrared spectrum of pure water.

Figure 2:
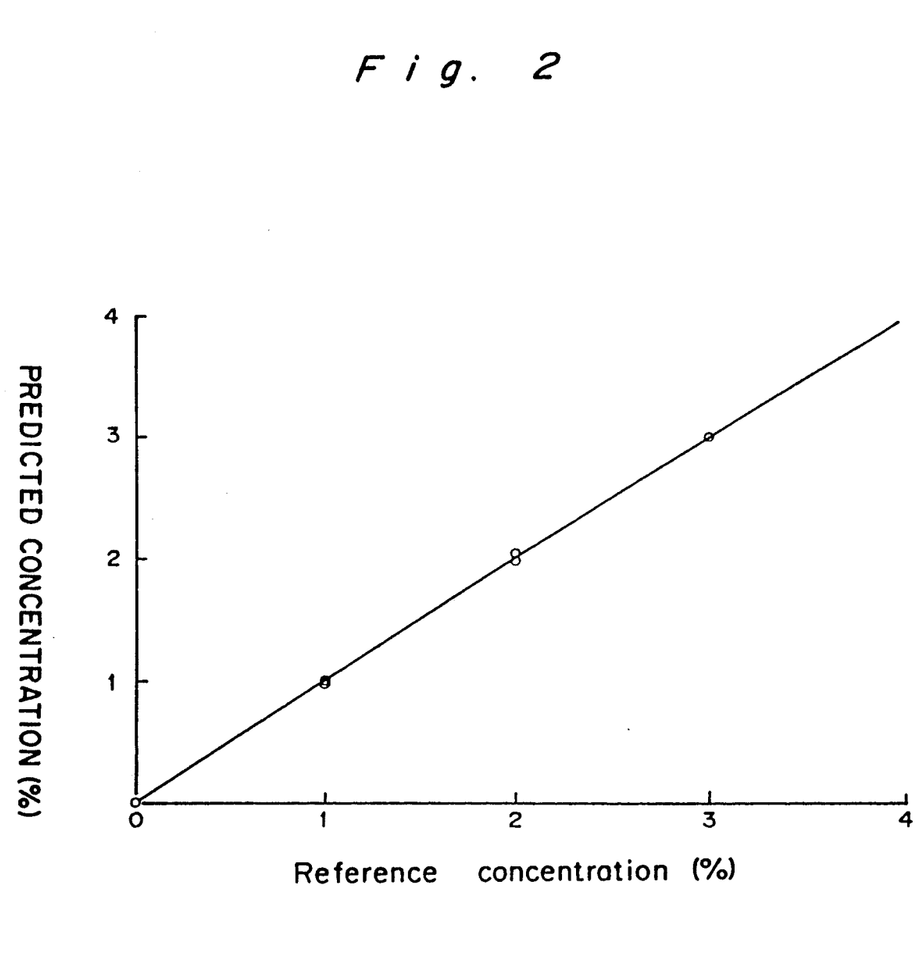
FIG. 2–FIG. 7 are graphs which show correlations between reference concentrations of various samples and predicted concentrations of the samples obtained by means of the calibration equation (I).
Figure 3:
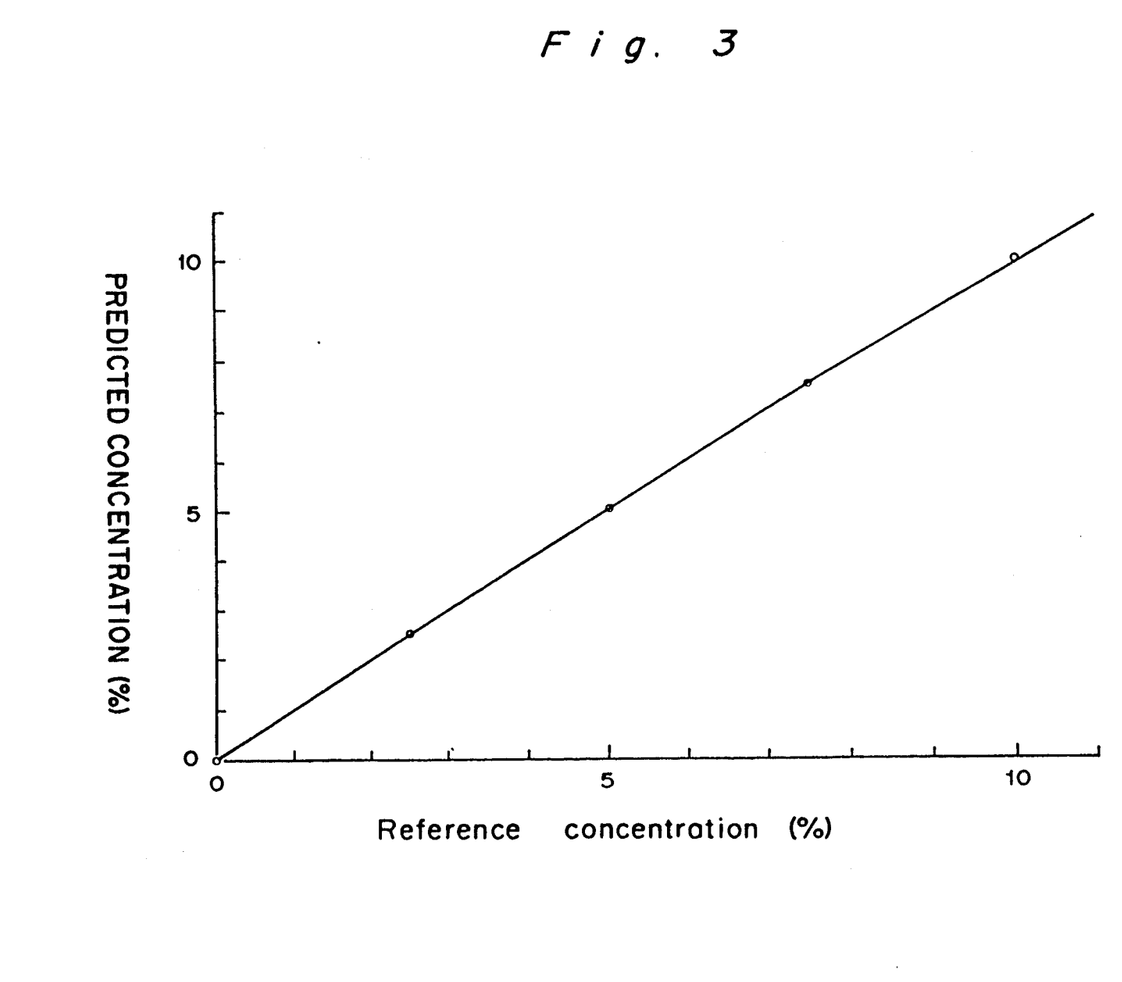
Figure 8:
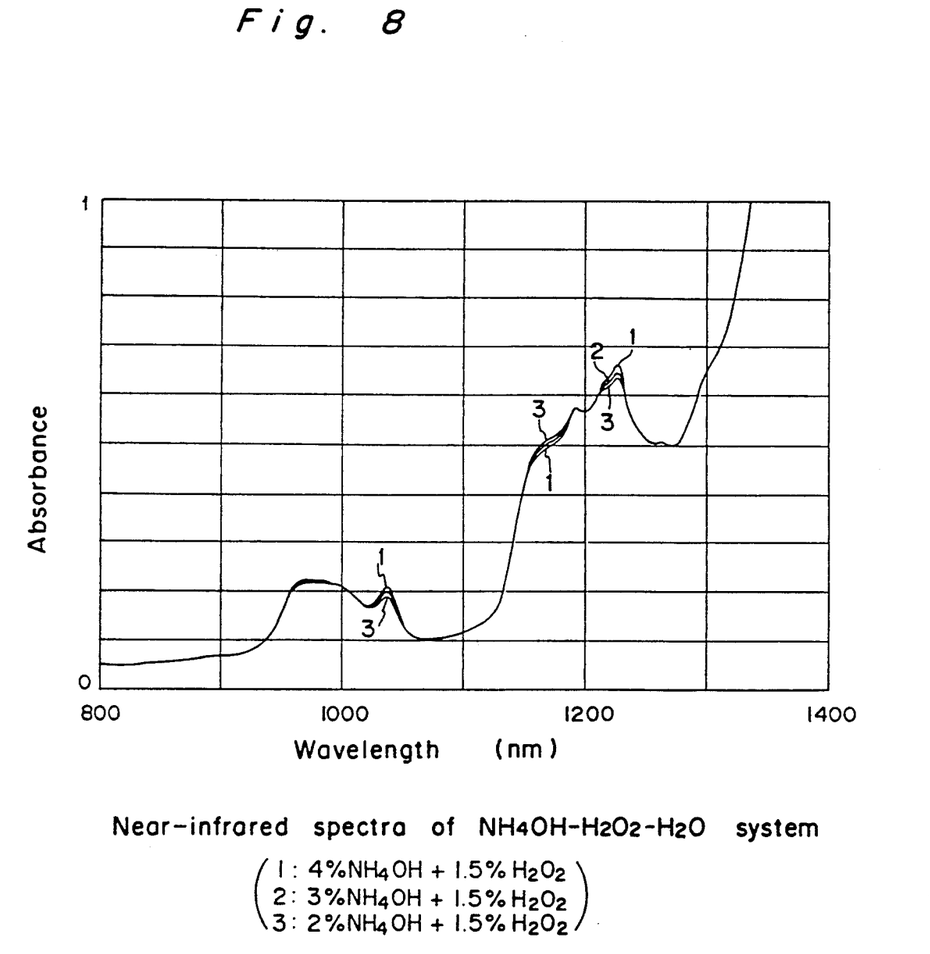
FIG. 8 and FIG. 9 are near-infrared spectra of $NH_4OH-H_2O_2-H_2O$ system.
Figure 9:
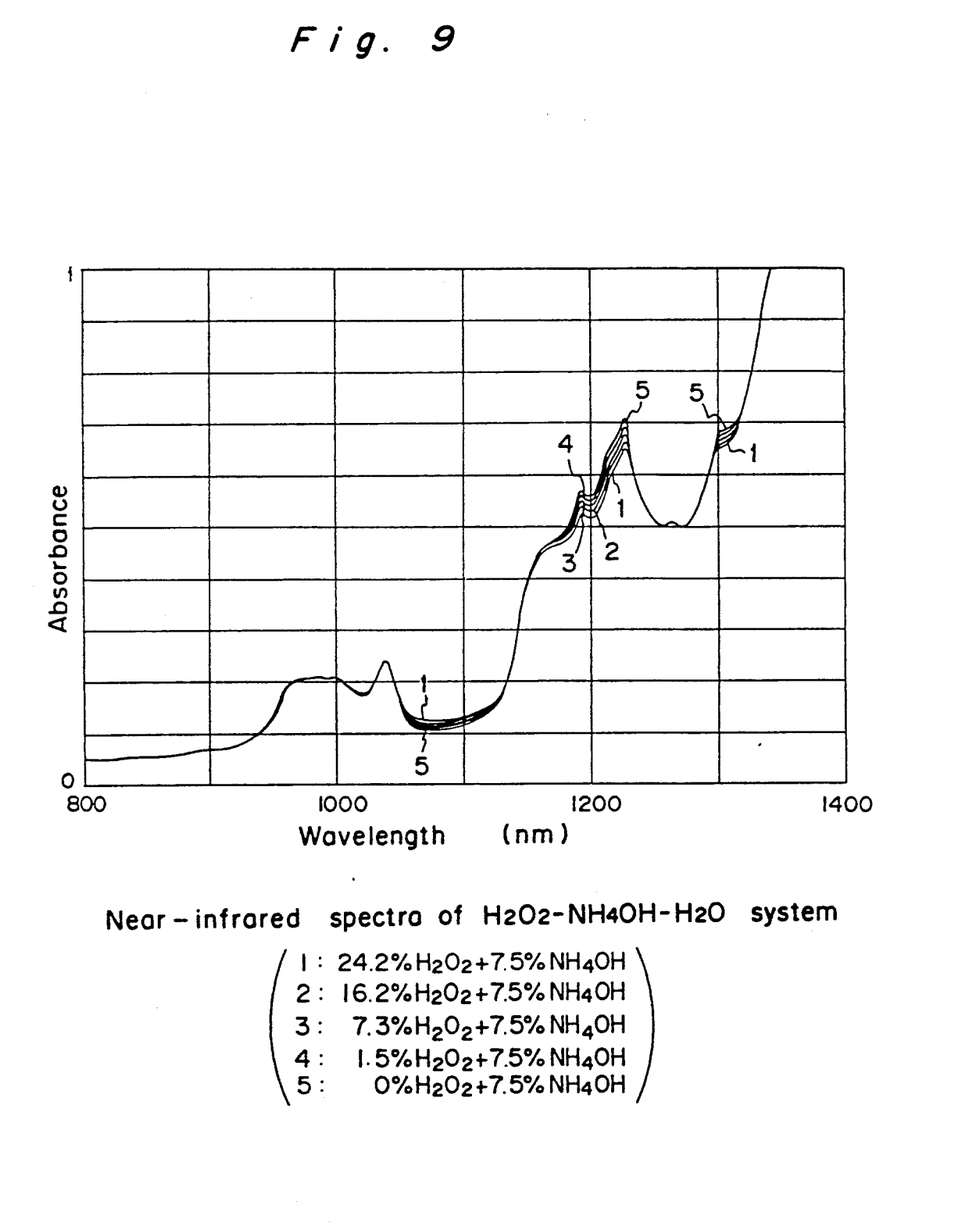

The wavelengths $\lambda_1-\lambda_6$ were selected by investigating the aforesaid difference spectra. In other words, the difference spectra of $NH_4OH$ and $H_2O_2$ were obtained based on the near-infrared spectrum shown in FIG. 8 (wherein the concentration of $H_2O_2$ is 1.5% and the concentrations of $NH_4OH$ are varied between 2-4%) and that shown in FIG. 9 (wherein the concentration of $NH_4OH$ of 7.5% and the concentrations of $H_2O_2$ are varied between 0-24.2 %) respectively and the following wavelengths at which characteristic difference spectra are given were selected:

For $NH_4OH$
$\lambda_1 = 980$ nm, $\lambda_2 = 1080$ nm, $\lambda_3 = 1150$ nm, $\lambda_4 = 1200$ nm, $\lambda_5 = 1250$ nm, $\lambda_6 = 1300$ nm
For $H_2O_2$
$\lambda_1 = 1050$ nm, $\lambda_2 = 1066$ nm, $\lambda_3 = 1070$ nm, $\lambda_4 = 1146$ nm, $\lambda_5 = 1191$ nm, $\lambda_6 = 1214$ nm Standard error of prediction Se (%) and coefficient of multiple determination $R^2$ concerning accuracy of the calibration equations and evaluation by the verification samples are as follows:

Accuracy of the calibration equations
For $NH_4OH$
$Se = 0.018\%, R^2 = 0.9999$
For $H_2O_2$
$Se = 0.012\%, R^2 = 0.9999$
Evaluation by the verification samples
For $NH_4OH$
$Se = 0.018\%, R^2 = 0.9999$
For $H_2O_2$
$Se = 0.017\%, R^2 = 0.9999$ Predicted concentrations obtained by the calibration equations and reference concentrations of the verification samples are shown in Table 1 as well as FIG. 2 for $NH_4OH$ and FIG. 3 for $H_2O_2$.

TABLE 1

| Sample No. | NH4OH | | | H2O2 | | |
|---|---|---|---|---|---|---|
| | Reference concentration | Predicted concentration | Difference | Reference concentration | Predicted concentration | Difference |
| 1 | 3.00 | 3.00 | 0.00 | 10.00 | 10.05 | −0.05 |
| 2 | 3.00 | 2.97 | 0.03 | 7.50 | 7.51 | −0.01 |
| 3 | 3.00 | 2.99 | 0.01 | 5.00 | 4.99 | 0.01 |
| 4 | 3.00 | 3.01 | −0.01 | 2.50 | 2.51 | −0.01 |
| 5 | 3.01 | 2.97 | 0.04 | 0.00 | −0.01 | 0.01 |
| 6 | 2.00 | 2.00 | 0.00 | 10.00 | 9.99 | 0.01 |
| 7 | 2.00 | 1.99 | 0.01 | 7.50 | 7.49 | 0.01 |

TABLE 1-continued

| Sample No. | NH₄OH Reference concentration | NH₄OH Predicted concentration | Difference | $H_2O_2$ Reference concentration | $H_2O_2$ Predicted concentration | Difference |
|---|---|---|---|---|---|---|
| 8 | 2.00 | 1.97 | 0.03 | 5.00 | 5.00 | 0.00 |
| 9 | 2.00 | 1.99 | 0.01 | 2.50 | 2.51 | −0.01 |
| 10 | 2.00 | 2.04 | −0.04 | 0.00 | 0.02 | −0.02 |
| 11 | 1.00 | 1.00 | 0.00 | 10.00 | 10.01 | −0.01 |
| 12 | 1.00 | 1.02 | −0.02 | 7.50 | 7.51 | −0.01 |
| 13 | 1.01 | 1.02 | −0.01 | 5.01 | 4.99 | 0.02 |
| 14 | 1.00 | 0.99 | 0.01 | 2.50 | 2.49 | 0.01 |
| 15 | 1.01 | 0.98 | 0.03 | 0.00 | 0.00 | 0.00 |
| 16 | 0.00 | −0.00 | 0.00 | 10.00 | 10.01 | 0.00 |
| 17 | 0.00 | 0.00 | 0.00 | 5.01 | 5.03 | 0.02 |
| 18 | 0.00 | −0.01 | 0.01 | 2.50 | 2.50 | 0.00 |

EXAMPLE 2

Quantitative determination of hydrochloric acid-hydrogen peroxide

An aqueous solution of mixture of hydrochloric acid and hydrogen peroxide ($HCl:H_2O_2:H_2O=1:1:5$) is a typical cleaning fluid which is used to remove heavy metals from silicon wafer.

Preparation of samples

In order to verify the practicability of the calibration equation for quantitative determination, calibration set of samples and verification set of samples were prepared whose concentrations encompass to the range used in the industrial process for cleaning semiconductor.

Twenty-two calibration samples and 22 verification samples, in which concentrations of HCl or $H_2O_2$ are 10-0 wt % and ratios of the components are different from each other, were prepared by diluting hydrochloric acid whose concentration (35.4%) is confirmed by titration using sodium hydroxide with hydrogen peroxide solution whose concentration (34.95%) is confirmed by titration using sodium thiosulfate.

Derivation of the calibration equation

A set of six wavelengths were selected from the range of 800-1400 nm which is optimum for the cell of which optical pass length is 10 mm in due consideration of the number of components of the samples, temperature variation and variable factors of the apparatus. The same set of six wavelengths was used in order to determine the concentration of HCl and $H_2O_2$ simultaneously.

The following calibration equations are obtained according to the aforementioned derivation procedure of the calibration equation.

For HCl
$C = 23.09A_1 + 62.25A_2 - 96.41A_3 + 58.90A_4 - 129.0A_5 + 85.7A_6$
For $H_2O_2$
$C = -3.21A_1 + 33.64A_2 + 97.22A_3 - 112A_4 + 88.02A_5 - 112.7A_6$

In the above calibration equations, $A_1$–$A_6$ are absorbances at wavelengths $\lambda_1$–$\lambda_6$ corresponding to the absorption bands which give significant differences in comparison with that of near-infrared spectrum of pure water. The following wavelengths were selected in accordance with the difference spectrum method as described in Example 1:

$\lambda_1 = 980$ nm, $\lambda_2 = 1040$ nm, $\lambda_3 = 1145$ nm, $\lambda_4 = 1190$ nm, $\lambda_5 = 1230$ nm, $\lambda_6 = 1300$ nm.

Se (%) and $R^2$ are as follows:

Accuracy of the calibration equations
For HCl
Se = 0.06%, $R^2$ = 0.9998
For $H_2O_2$
Se = 0.10%, $R^2$ = 0.9996
Evaluation by the verification samples
For HCl
Se = 0.07%, $R^2$ = 0.9998
For $H_2O_2$
Se = 0.13%, $R^2$ = 0.9994

Figure 4:
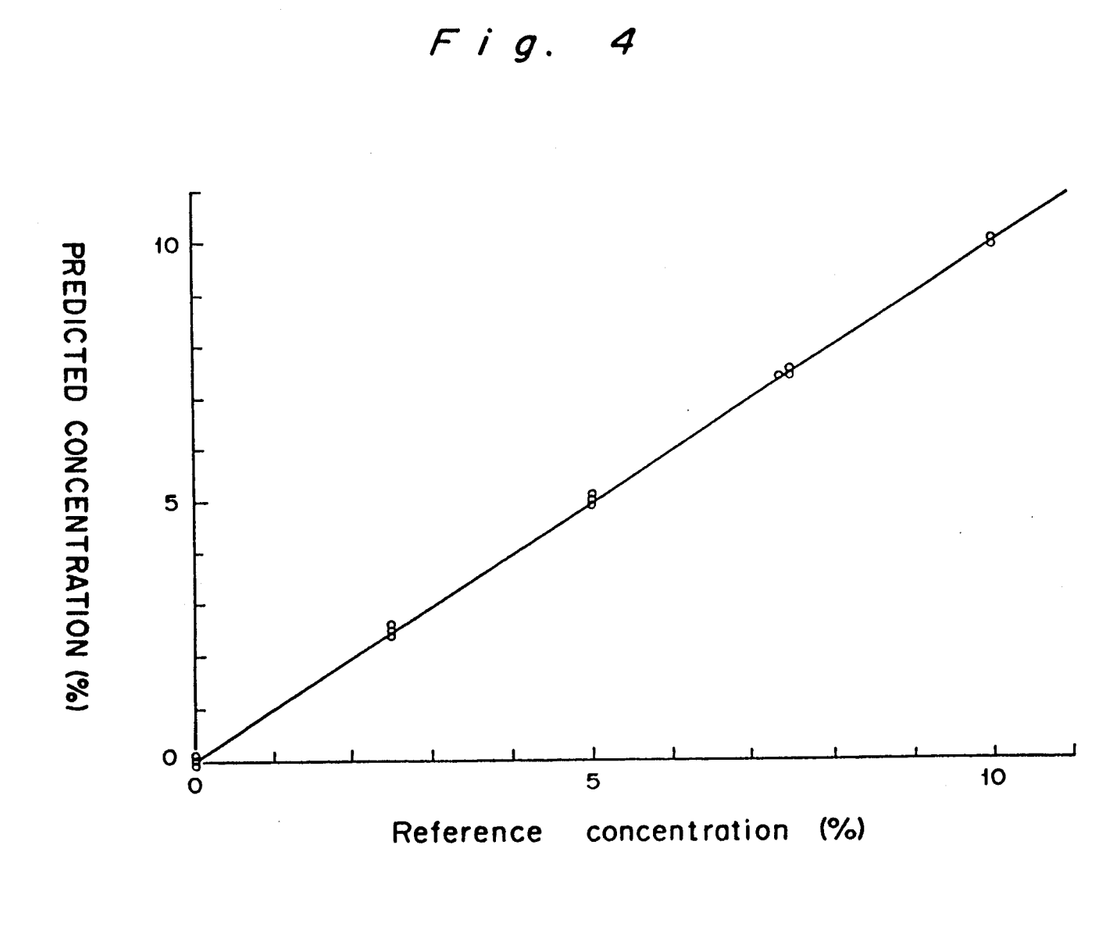
Figure 5:
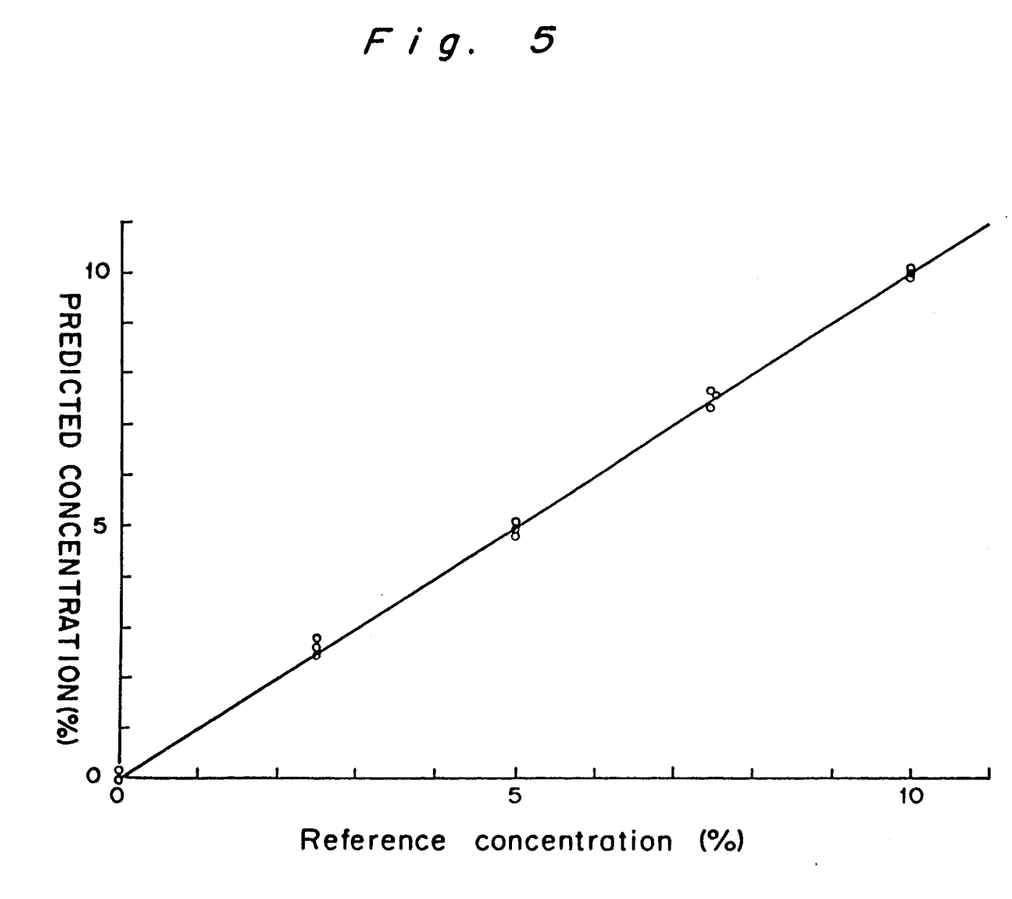

Predicted concentrations obtained by the calibration equations and reference concentrations of the samples are shown in Table 2 as well as FIG. 4 for HCl and FIG. 5 for $H_2O_2$.

TABLE 2

| Sample No. | NH₄OH Reference concentration | NH₄OH Predicted concentration | Difference | $H_2O_2$ Reference concentration | $H_2O_2$ Predicted concentration | Difference |
|---|---|---|---|---|---|---|
| 1 | 10.00 | 10.04 | −0.04 | 10.00 | 9.90 | 0.10 |
| 2 | 10.00 | 9.93 | 0.07 | 7.50 | 7.65 | −0.15 |
| 3 | 10.00 | 10.01 | −0.01 | 5.00 | 4.94 | −0.04 |
| 4 | 10.00 | 9.95 | 0.05 | 2.50 | 2.61 | −0.11 |
| 5 | 10.00 | 10.02 | −0.02 | 0.00 | −0.04 | 0.04 |
| 6 | 7.50 | 7.52 | −0.02 | 10.00 | 9.94 | 0.06 |
| 7 | 7.37 | 7.38 | −0.01 | 7.58 | 7.54 | 0.04 |
| 8 | 7.50 | 7.44 | 0.06 | 5.00 | 5.09 | −0.09 |
| 9 | 7.50 | 7.53 | −0.03 | 2.50 | 2.42 | 0.08 |
| 10 | 7.50 | 7.42 | 0.08 | 0.00 | 0.12 | −0.12 |
| 11 | 5.00 | 4.96 | 0.04 | 10.01 | 10.08 | −0.07 |
| 12 | 5.00 | 5.12 | −0.12 | 7.50 | 7.29 | 0.21 |
| 13 | 5.00 | 5.06 | −0.06 | 5.00 | 4.91 | 0.09 |
| 14 | 5.00 | 4.87 | 0.13 | 2.50 | 2.80 | −0.30 |

TABLE 2-continued

| Sample No. | NH₄OH | | | H₂O₂ | | |
|---|---|---|---|---|---|---|
| | Reference concentration | Predicted concentration | Difference | Reference concentration | Predicted concentration | Difference |
| 15 | 5.00 | 5.06 | −0.06 | 0.00 | −0.08 | 0.08 |
| 16 | 2.50 | 2.47 | 0.03 | 10.00 | 10.02 | −0.02 |
| 17 | 2.50 | 2.61 | −0.11 | 5.00 | 4.76 | 0.24 |
| 18 | 2.50 | 2.48 | 0.02 | 2.50 | 2.50 | 0.00 |
| 19 | 2.50 | 2.41 | 0.09 | 0.00 | 0.16 | −0.16 |
| 20 | 0.00 | 0.08 | −0.08 | 10.00 | 9.86 | 0.14 |
| 21 | 0.00 | −0.11 | 0.11 | 7.49 | 7.64 | −0.15 |
| 22 | 0.00 | −0.03 | 0.03 | 5.00 | 5.04 | −0.04 |

EXAMPLE 3

Quantitative determination of sulfuric acid-hydrogen peroxide

An aqueous solution of mixture of sulfuric acid-hydrogen peroxide is a cleaning fluid which is used to remove heavy metals from silicon wafer, said heavy metals being oxidized to ions which are soluble in the cleaning fluid.

Preparation of samples

In order to verify the performance of the calibration equation for quantitative determination, calibration set of samples and verification set of samples were prepared whose concentrations encompass to the range used in the industrial process for cleaning semiconductor.

Thirty calibration samples and 30 verification samples, in which concentrations of $H_2SO_4$ and $H_2O_2$ are 0-97 wt % and 0-34.95 wt % respectively and ratios of the components are different from each other, were prepared by diluting sulfuric acid whose concentration (97%) is confirmed by titration using sodium hydroxide with hydrogen peroxide solution whose concentration (34.95%) is confirmed by titration using sodium thiosulfate.

Derivation of the calibration equation

A set of six wavelengths were selected from the range of 800–1400 nm as in the case of Example 1.

The following calibration equations are obtained according to the aforementioned derivation procedure of the calibration equation:

For $H_2SO_4$
$C = 18.14 A_1 + 50.31 A_2 - 48.21 A_3 + 102.3 A_4 - 150.0 A_5 + 53.2 A_6$
For $H_2O_2$
$C = -10.10 A_1 + 40.21 A_2 + 38.26 A_3 - 130.0 A_4 + 70.26 A_5 - 130.2 A_6$

In the above calibration equations, $A_1$–$A_6$ are absorbances at wavelengths $\lambda_1$–$\lambda_6$ corresponding to the absorption bands which give siginificant difference in comparison with that of near-infrared spectrum of pure water.

Figure 10:
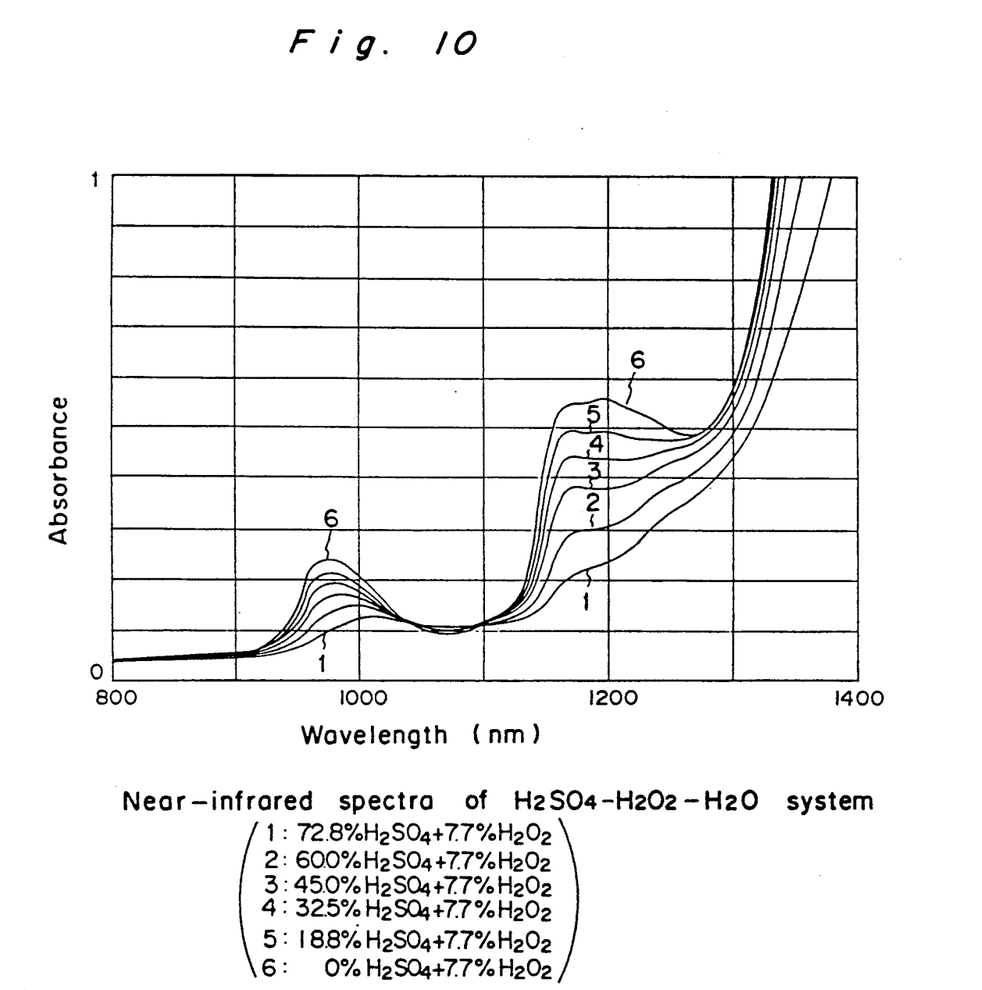
FIG. 10 and FIG. 11 are near-infrared spectra of $H_2SO_4-H_2O_2-H_2O$ system.
Figure 11:
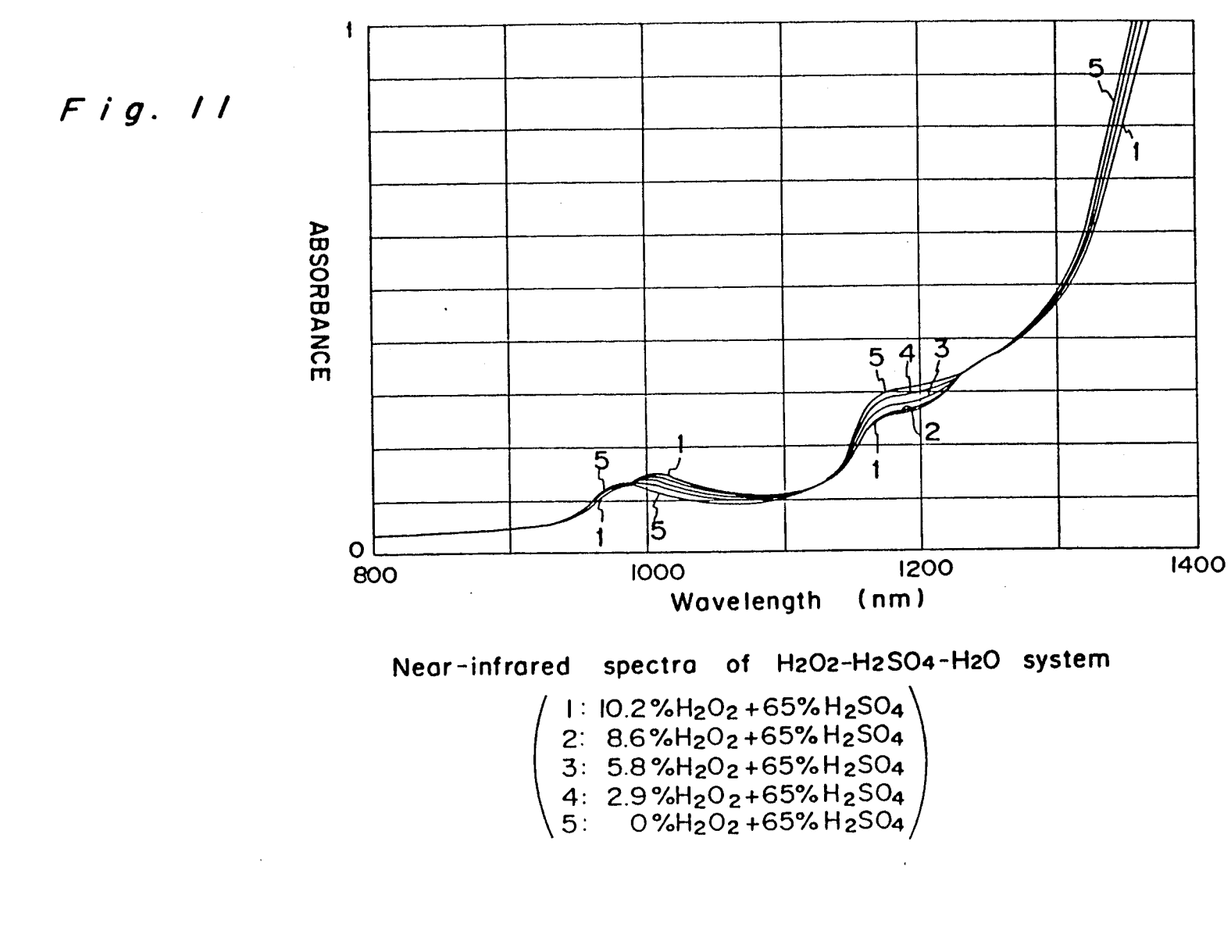

These wavelengths $\lambda_1$–$\lambda_6$ were selected by investigating the aforesaid difference spectra. In other words, the differences spectra of $H_2SO_4$ and $H_2O_2$ were obtained based on the near-infrared spectrum shown in FIG. 10 (wherein the concentration of $H_2O_2$ is 7.7% and the concentration of $H_2SO_4$ are varied between 0–72.8%) and that shown in FIG. 11 (wherein the concentration of $H_2SO_4$ is 65% and the concentrations of $H_2O_2$ are varied between 0–10.2%) respectively and the following wavelengths at which characteristic difference spectra are given were selected:

$\lambda_1 = 980$ nm, $\lambda_2 = 1040$ nm, $\lambda_3 = 1145$ nm, $\lambda_4 = 1190$ nm, $\lambda_5 = 1230$ nm, $\lambda_6 = 1300$ nm.

Se (%) and $R^2$ are as follows:

Accuracy of the calibration equations
For $H_2SO_4$
Se = 0.15%, $R^2$ = 0.99997
For $H_2O_2$
Se = 0.18%, $R^2$ = 0.9995
Evaluation by the verification samples
For $H_2SO_4$
Se = 0.29%, $R^2$ = 0.99989
For $H_2O_2$
Se = 0.20%, $R^2$ = 0.9994

Figure 6:
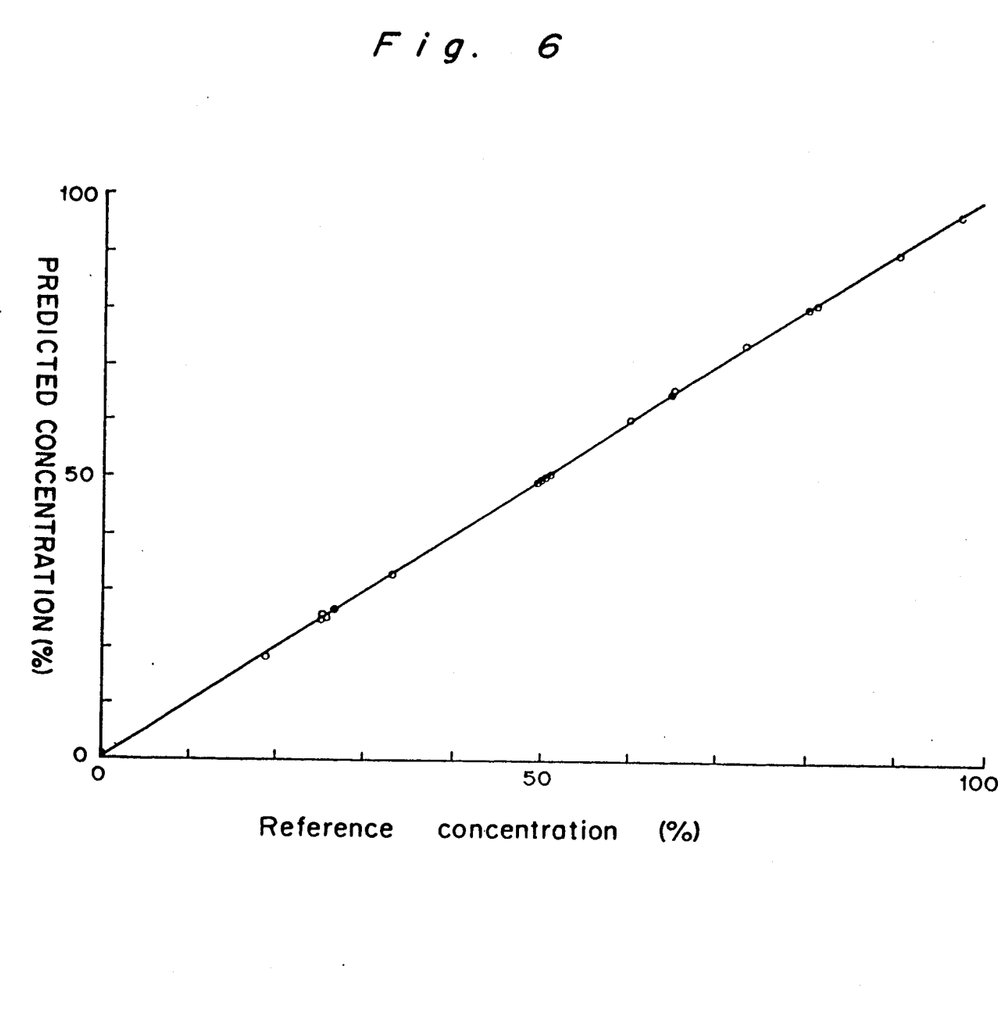
Figure 7:
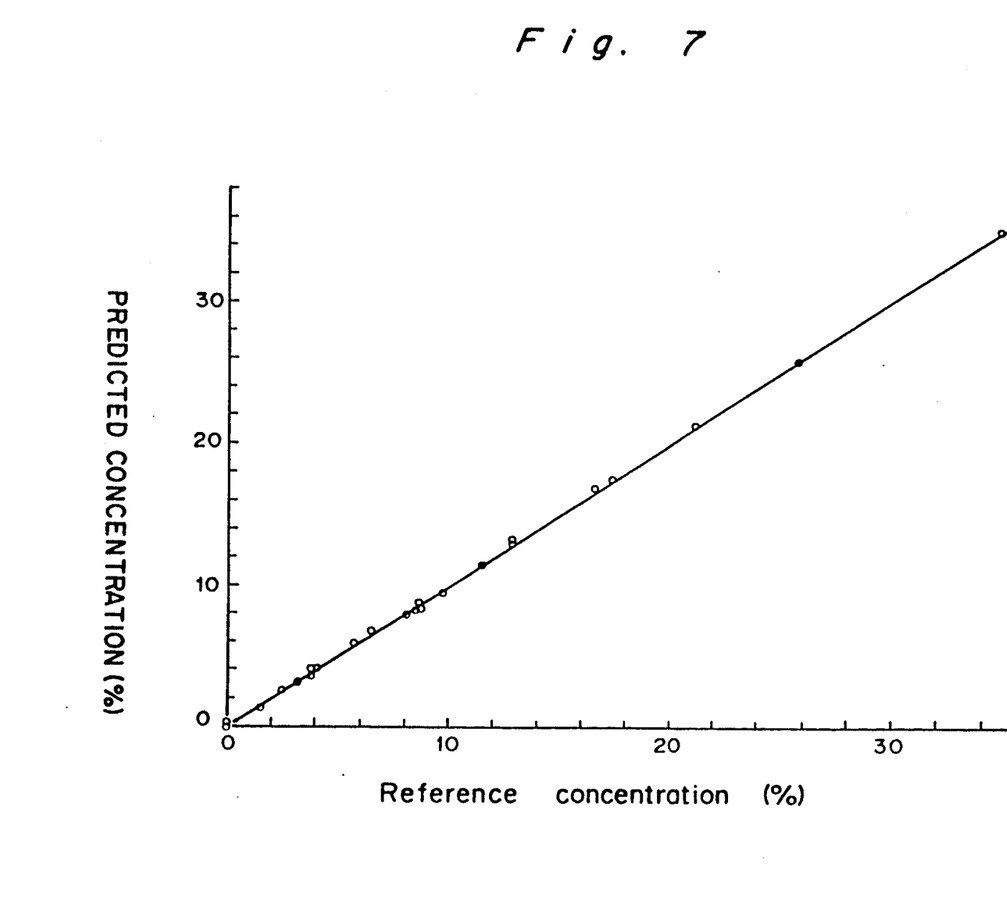

Predicted concentrations obtained by the calibration equations and reference concentrations of the samples are shown in Table 3 as well as FIG. 6 for $H_2SO_4$ and FIG. 7 for $H_2O_2$.

TABLE 3

| Sample No. | NH₄OH | | | H₂O₂ | | |
|---|---|---|---|---|---|---|
| | Reference concentration | Predicted concentration | Difference | Reference concentration | Predicted concentration | Difference |
| 1 | 0.00 | −0.08 | 0.08 | 8.74 | 8.74 | 0.00 |
| 2 | 0.00 | −0.15 | 0.15 | 17.48 | 17.55 | −0.07 |
| 3 | 0.00 | 0.62 | −0.62 | 34.95 | 35.09 | −0.14 |
| 4 | 18.80 | 18.19 | 0.61 | 8.76 | 8.34 | 0.42 |
| 5 | 24.96 | 25.02 | −0.06 | 0.00 | −0.27 | 0.27 |
| 6 | 26.47 | 26.70 | −0.23 | 4.11 | 4.10 | 0.01 |
| 7 | 25.11 | 25.76 | −0.65 | 12.95 | 12.94 | 0.01 |
| 8 | 25.56 | 25.41 | 0.15 | 21.20 | 21.32 | −0.12 |
| 9 | 25.14 | 25.76 | −0.62 | 25.89 | 25.75 | 0.14 |
| 10 | 33.08 | 32.97 | 0.11 | 8.58 | 8.84 | −0.26 |
| 11 | 49.27 | 49.09 | 0.18 | 8.46 | 8.25 | 0.21 |
| 12 | 50.13 | 50.40 | −0.27 | 0.00 | 0.22 | −0.22 |
| 13 | 50.75 | 50.70 | 0.05 | 3.83 | 3.61 | 0.22 |
| 14 | 49.94 | 49.77 | 0.17 | 8.10 | 7.89 | 0.21 |
| 15 | 50.45 | 50.51 | −0.06 | 12.91 | 13.23 | −0.32 |

TABLE 3-continued

| Sample No. | NH₄OH Reference concentration | NH₄OH Predicted concentration | Difference | H₂O₂ Reference concentration | H₂O₂ Predicted concentration | Difference |
|---|---|---|---|---|---|---|
| 16 | 50.83 | 50.76 | 0.07 | 16.64 | 16.83 | −0.19 |
| 17 | 60.13 | 60.40 | −0.27 | 8.68 | 8.80 | −0.12 |
| 18 | 65.00 | 64.79 | 0.21 | 0.00 | −0.03 | 0.03 |
| 19 | 65.27 | 65.60 | −0.33 | 3.22 | 3.13 | 0.09 |
| 20 | 65.09 | 64.92 | 0.17 | 6.51 | 6.82 | −0.31 |
| 21 | 64.99 | 65.23 | −0.24 | 9.71 | 9.52 | 0.19 |
| 22 | 64.96 | 64.73 | 0.23 | 11.55 | 11.49 | 0.06 |
| 23 | 73.29 | 73.63 | −0.34 | 8.54 | 8.13 | 0.41 |
| 24 | 80.00 | 79.96 | 0.04 | 0.00 | 0.02 | −0.02 |
| 25 | 80.02 | 80.32 | −0.30 | 1.53 | 1.28 | 0.25 |
| 26 | 80.00 | 80.00 | 0.00 | 3.88 | 4.05 | −0.17 |
| 27 | 80.99 | 80.92 | 0.07 | 5.77 | 5.87 | −0.10 |
| 28 | 90.00 | 89.75 | 0.25 | 0.00 | −0.07 | 0.07 |
| 29 | 90.02 | 90.20 | −0.18 | 2.51 | 2.48 | −0.03 |
| 30 | 97.00 | 97.08 | −0.08 | 0.00 | 0.11 | −0.11 |

EXAMPLE 4

Quantitative determination of sodium hypochlorite
Preparation of samples

Although an analysis object in this example is a concentration of $ClO^-$ in an aqueous solution of sodium hypochlorite, 13 samples were prepared by changing the concentration with combinations of ion pairs in due consideration of disturbance and interference of coexisting ionic species such as $Na^+$, $Cl^-$, $CO_3^-$, and $OH^-$. The concentration of $ClO^-$ was confirmed by titration using sodium thiosulfate after excess amount of acetic acid and more than equivalent weight of potassium iodide were added to the aqueous solution of NaClO. Concentrations of the coexisting ions were determined by an electrochemical method.

Derivation of the calibration equation

The following calibration equations are obtained according to the aforementioned derivation procedure of the calibration equation:

$$C = 20.07A_1 + 1634A_2 - 849.0A_3 - 770.2A_4 - 430.9A_5 + 103.3A_6 + 388.7.$$

In this calibration equation, $A_1-A_6$ are absorbances at wavelengths $\lambda_1-\lambda_6$ corresponding to the absorption bands which give significant differences in comparison with that of near-infrared spectrum of pure water.

The following wavelengths $\lambda_1-\lambda_6$ were selected by the aforesaid difference spectra method:

$\lambda_1 = 1005$ nm, $\lambda_2 = 1143$ nm, $\lambda_3 = 1167$ nm, $\lambda_4 = 1255$ nm, $\lambda_5 = 1300$ nm, $\lambda_6 = 1350$ nm.

Se (%) and $R^2$ are as follows:

| Accuracy of the calibration equations |
|---|
| Se = 0.089%, $R^2$ = 0.9998 |

Figure 12:
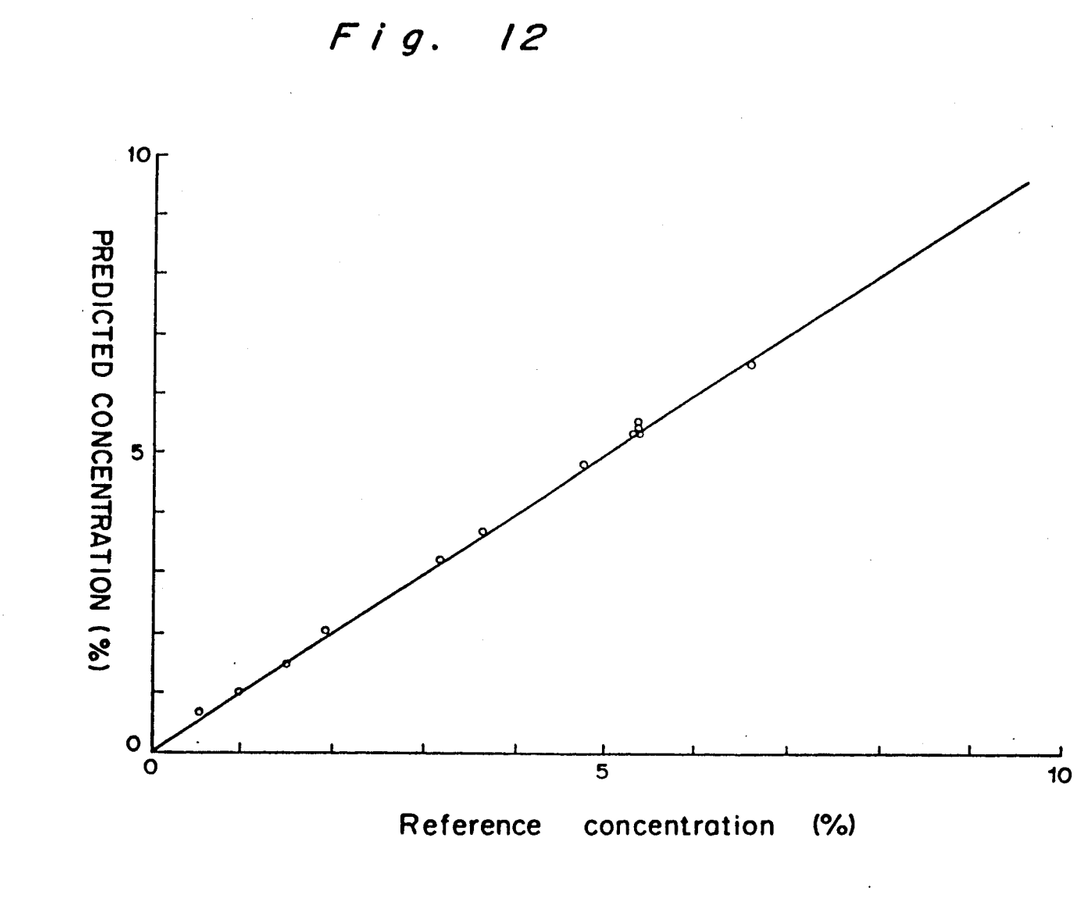
FIG. 12 is a graph of predicted concentrations obtained by the calibration equations and reference concentrations of the samples shown in Table 4.

Predicted concentrations obtained by the calibration equations and reference concentrations of the samples are shown in Table 4 and FIG. 12.

TABLE 4

| Sample No. | Reference concentration | Predicted concentration | Difference |
|---|---|---|---|
| 1 | 5.35 | 5.41 | −0.06 |
| 2 | 5.37 | 5.32 | 0.05 |
| 3 | 5.31 | 5.31 | 0.00 |
| 4 | 5.35 | 5.51 | −0.16 |
| 5 | 6.59 | 6.47 | 0.12 |

TABLE 4-continued

| Sample No. | Reference concentration | Predicted concentration | Difference |
|---|---|---|---|
| 6 | 3.62 | 3.67 | −0.05 |
| 7 | 1.50 | 1.47 | 0.03 |
| 8 | 4.75 | 4.80 | −0.05 |
| 9 | 3.16 | 3.20 | −0.04 |
| 10 | 3.16 | 3.18 | −0.02 |
| 11 | 1.93 | 2.03 | −0.10 |
| 12 | 0.99 | 1.00 | −0.01 |
| 13 | 0.55 | 0.67 | −0.12 |

What is claimed is:

1. A method of determining quantitatively the concentration of an inorganic electrolyte in an aqueous solution used in processing a semiconductor and containing at least one inorganic electrolyte, said method comprising carrying out the following steps for each inorganic electrolyte:

(i) obtaining a near-infrared spectrum at 800–1400 nm of an aqueous solution of a known concentration of said electrolyte;

(ii) selecting from the spectrum obtained in step (i) at least three wavelengths at which there are observed significant differences between said spectrum and the near-infrared spectrum of pure water at 800–1400 nm, said differences being caused by ionic hydration;

(iii) repeating step (i) for a plurality of aqueous solutions each containing a known concentration of said electrolyte;

(iv) deriving a calibration equation (I) for said electrolyte by regression analysis of the relation between the concentration of electrolyte in the aqueous solutions used in steps (i) and (iii) and the absorbance at each of the wavelengths selected in step (ii):

$$C = \Sigma a_i A_i \quad (I)$$

wherein C is the concentration of said electrolyte, $A_i$ is the absorbance at each of said selected wavelengths, and $a_i$ is a constant determined for each of said selected wavelengths by said regression analysis;

(v) obtaining a near-infrared spectrum under the same conditions as in step (i) for a sample of unknown concentration of said electrolyte;

(vi) measuring the absorbance at each of said selected wavelengths in the spectrum obtained in step (v); and (vii) determining the concentration of said electrolyte in the sample of unknown concentration by correlation between the absorbances measured in step (vi) and the calibration equation obtained in step (iv).

2. A quantitative determination method according to claim 1, wherein said inorganic electrolyte is any one or more of the electrolytes selected from the group consisting of a mixture of ammonia and hydrogen peroxide, a mixture of hydrochloric acid and hydrogen peroxide, a mixture of sulfuric acid and hydrogen peroxide, hydrofluoric acid, a mixture of hydrochloric acid and nitric acid, a mixture of hydrofluoric acid and ammonium fluoride, and sodium hypochlorite.

* * * * *